US012594003B2

(12) United States Patent
Lorato et al.

(10) Patent No.: US 12,594,003 B2
(45) Date of Patent: Apr. 7, 2026

(54) DEVICE, SYSTEM AND METHOD FOR DETERMINING RESPIRATORY INFORMATION OF A SUBJECT

(71) Applicant: KONINKLIJKE PHILIPS N.V., Eindhoven (NL)

(72) Inventors: Ilde Lorato, Eindhoven (NL); Gerard de Haan, Helmond (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 18/292,170

(22) PCT Filed: Jul. 19, 2022

(86) PCT No.: PCT/EP2022/070258
§ 371 (c)(1),
(2) Date: Jan. 25, 2024

(87) PCT Pub. No.: WO2023/006525
PCT Pub. Date: Feb. 2, 2023

(65) Prior Publication Data
US 2024/0285188 A1 Aug. 29, 2024

(30) Foreign Application Priority Data

Jul. 26, 2021 (EP) .................................... 21187786

(51) Int. Cl.
*A61B 5/087* (2006.01)
*A61B 5/01* (2006.01)
(Continued)

(52) U.S. Cl.
CPC ................ *A61B 5/087* (2013.01); *A61B 5/01* (2013.01); *A61B 5/1128* (2013.01); *A61B 5/113* (2013.01);
(Continued)

(58) Field of Classification Search
None
See application file for complete search history.

(56) References Cited

U.S. PATENT DOCUMENTS

| | | |
|---|---|---|
| 8,149,273 B2 | 4/2012 | Liu |
| 10,165,971 B2 | 1/2019 | Omi |

(Continued)

FOREIGN PATENT DOCUMENTS

| | | |
|---|---|---|
| GB | 2571147 A | 8/2019 |
| JP | 2009183560 A | 8/2009 |

(Continued)

OTHER PUBLICATIONS

International Search Report and Written Opinion for PCT/EP2022/070258; Mailing date.
(Continued)

*Primary Examiner* — Yi-Shan Yang

(57) ABSTRACT

The present invention relates to a device, system and method for determining respiratory information of a subject. The device comprises an image input (21) configured to obtain thermal images of the subject, processing unit (22) configured to determine respiratory information of the subject from the thermal images, and an output (23) configured to output the determined respiratory information of the subject. The processing unit (22) is configured to determine the respiratory information of the subject by identifying in the obtained thermal images respiratory pixels and/or pixel groups that show temperature variations related to respiration, determining, from among the respiratory pixels and/or pixel groups, respiratory flow pixels and/or pixel groups that show respiratory flow, wherein one or more spatial filters are applied to the respiratory pixels and/or pixel groups to discriminate the respiratory flow pixels and/or pixel groups from respiratory motion pixels and/or pixel groups that show respiratory motion, and determining respiratory information (Continued)

of the subject from the respiratory flow pixels and/or pixel groups and/or the respiratory motion pixels and/or pixel groups.

20 Claims, 7 Drawing Sheets

(51) Int. Cl.

| | | |
|---|---|---|
| *A61B 5/11* | (2006.01) | |
| *A61B 5/113* | (2006.01) | |
| *G06T 7/00* | (2017.01) | |
| *G06T 7/246* | (2017.01) | |

(52) U.S. Cl.

CPC ............ *G06T 7/0012* (2013.01); *G06T 7/246* (2017.01); *G06T 2207/10048* (2013.01); *G06T 2207/30004* (2013.01)

(56) References Cited

U.S. PATENT DOCUMENTS

| | | | | |
|---|---|---|---|---|
| 11,607,160 | B2 * | 3/2023 | Cuestas Rodriguez ...................... | |
| | | | | A61B 5/377 |
| 2014/0236036 | A1 | 8/2014 | de Haan et al. | |
| 2014/0275832 | A1 | 9/2014 | Muehlsteff et al. | |
| 2020/0397349 | A1 | 12/2020 | Fornell | |
| 2021/0212595 | A1 * | 7/2021 | Mills .................... | A61B 5/1176 |

FOREIGN PATENT DOCUMENTS

| | | | | |
|---|---|---|---|---|
| KR | 102054213 | B1 * | 6/2019 | |
| KR | 20190060243 | A | 6/2019 | |

OTHER PUBLICATIONS

Lorato, I. et al., "Multi-Camera Infrared Thermography for Infant Respiration Monitoring," Biomedical Optics Express, 2020, vol. 11, No. 9, 14 pages.

Mcnellis, R.J. et al., "Screening for Obstructive Sleep Apnea in Adults," Am. Fam. Physician, 2017, vol. 96, No. 2, pp. 123-124.

Eichenwald, E. C., "Apnea of Prematurity," Pediatrics, 2016, vol. 137, No. 1, 7 pages.

Javaheri, s. et al., "Sleep Apnea: Types, Mechanisms, and Clinical Cardiovascular Consequences," J. Am. Coll. Cardiol., 2017, vol. 69, No. 7, pp. 841-858.

Scebba, G. et al., "Multispectral Video Fusion for Non-Contact Monitoring of Respiratory Rate and Apnea," IEEE Transactions on Biomedical Engineering, 2021, vol. 68, No. 1, pp. 350-359.

Pereira, C.B. et al., "Estimation of Breathing Rate in Thermal Imaging Videos: a Pilot Study on Healthy Human Subjects", J Clin Monit Comput., 2017, vol. 31, No. 6, pp. 1241-1254.

Hu, M.H. et al., "Synergetic Use of Thermal and Visible Imaging Techniques for Contactless and Unobtrusive Breathing Measurement," Journal of Biomedical Optics, 2017, vol. 22, Issue 3, 11 pages.

Pereira, C.B. et al., "Noncontact Monitoring of Respiratory Rate in Newborn Infants Using Thermal Imaging," IEEE Transactions on Biomedical Engineering, 2019, vol. 66, No. 4, pp. 1105-1114.

Janssen, R. et al., "Video-Based Respiration Monitoring with Automatic Region of Interest Detection," Physiol Meas, 2016, vol. 37, No. 1, pp. 100-114.

Cho, Y. et al., "Robust Tracking of Respiratory Rate in High-Dynamic Range Scenes Using Mobile Thermal Imaging," Biomed Opt Express, 2017, vol. 8, No. 10, pp. 4480-4503.

Lorato, I. et al., "Camera-Based On-Line Short Cessation of Breathing Detection," 2019 IEEE/CVF International Conference on Computer Vision Workshop (ICCVW), 2019, pp. 1656-1663.

Martin, R., "Pathophysiology of Apnea of Prematurity," Fetal and Neonatal Physiology, 2017, 5th Edition, vol. 2, Chapter 157, 10 pages.

* cited by examiner

DEVICE, SYSTEM AND METHOD FOR DETERMINING RESPIRATORY INFORMATION OF A SUBJECT

This application is the U.S. National Phase application under 35 U.S.C. § 371 of International Application No. PCT/EP2022/070258, filed on Jul. 19, 2022, which claims the benefit of European Application 21187786.5, filed Jul. 26, 2021. These applications are hereby incorporated by reference herein.

FIELD OF THE INVENTION

The present invention relates to a device, system and method for determining respiratory information of a subject, in particular of a human being or an animal.

BACKGROUND OF THE INVENTION

The respiration rate (RR) is one of the most crucial vital signs, deterioration of which can indicate immediate action is required. Although subject motion usually shows signs of breathing, it is the flow, which is the most informative measurement, as respiratory motion may continue in case of an airway obstruction, as in e.g. sleep apnea. Measuring these apnea events unobtrusively during sleep is a currently unmet need.

Apnea is defined as a cessation of breathing lasting at least 20 s or 10 s if accompanied by bradycardia and/or desaturation in the infants' case, and it is generally referred to as apnea of prematurity. In adults, the term sleep disordered breathing is commonly used to include apnea occurrences and hypopneas.

In Neonatal Intensive Care Units (NICUs) the standard method to monitor respiration is chest impedance or impedance pneumography. The gold standard for adults is instead polysomnography (PSG). This requires the use of several sensors to accurately monitor the patient's vital signs. During PSG both respiratory flow and motion are monitored, using a thermistor close to the nostrils and/or mouth and two belts, thoracic and abdominal, to monitor respiration movements.

The need to monitor both respiratory flow and motion is caused by differences in specific types of apnea. Apneas can be generally separated both in infants and in adults in central apnea, obstructive apnea, and mixed apnea. Central apnea results in complete absence of respiration, visible thus, in both respiratory flow and motion. Obstructive apnea is a type of apnea during which still an effort to breathe is noticeable, but flow is completely absent. Mixed apnea is a mixture of the other two apneas. To detect and classify the type of apnea, both respiratory flow and respiratory motion need to be monitored.

Currently available methods and techniques to monitor respiration are, however, obtrusive and can cause discomfort and skin irritation and disturb the patient's sleep. Therefore, unobtrusive solutions are being considered as substitute to the contact methods. Within the category of unobtrusive technologies, the use of a thermal camera is the only one able to monitor both respiratory flow and motion, whereas respiratory motion can be detected using different imaging technologies in visible light, near-infrared (NIR) and using radar.

A thermal camera can be an alternative to contact monitoring methods for respiratory flow and motion. However, to obtain a respiratory flow signal, which will allow detect apneas, body landmark detection is typically needed. Known solutions separate contributions from thermal respiratory flow and motion. These require body parts detection using a thermal camera only or by combining it with another type of camera, such as an RBG or NIR camera. The detection of specific body parts is quite complex and likely too fragile to rely on in hospital environments. The presence of a blanket or a sheet covering the body and the several sleeping positions add to this complexity in the adults' case and even more so in the infants' case.

Solutions to automatically select the pixels containing respiratory information in cameras have been proposed to avoid the identification of landmarks. These methods are though unable to distinguish respiratory flow and motion contributions when used on thermal videos. Therefore, the output will be a mixture of flow and motion signals, which does not allow to accurately identify apneas.

LORATO ILDE ET AL: "Multi-camera infrared thermography for infant respiration monitoring", BIOMEDICAL OPTICS EXPRESS, vol. 11, no. 9, 1 Sep. 2020, discloses an algorithm to merge multiple thermal camera views and automatically detect the pixels containing respiration motion or flow using three features.

SUMMARY OF THE INVENTION

It is an object of the present invention to provide a device, system and method for determining respiratory information of a subject in an unobtrusive and accurate manner.

In a first aspect of the present invention a device for determining respiratory information of a subject is presented comprising:

an image input configured to obtain thermal images of the subject, the thermal images showing at least part of the subject's facial area and/or its surrounding;

a processing unit configured to determine respiratory information of the subject from the thermal images; and an output configured to output the determined respiratory information of the subject, wherein the processing unit is configured to determine the respiratory information of the subject by:

identifying in the obtained thermal images respiratory pixels and/or pixel groups that show temperature variations related to respiration, determining, from among the respiratory pixels and/or pixel groups, respiratory flow pixels and/or pixel groups that show respiratory flow, wherein one or more spatial filters are applied to the respiratory pixels and/or pixel groups to discriminate the respiratory flow pixels and/or pixel groups from respiratory motion pixels and/or pixel groups that show respiratory motion, and determining respiratory information of the subject from the respiratory flow pixels and/or pixel groups and/or the respiratory motion pixels and/or pixel groups.

In a further aspect of the present invention a system for determining respiratory information of a subject is presented comprising:

a thermal sensor unit configured to acquire thermal images of the subject, the thermal images showing at least part of the subject's facial area and/or its surrounding;

a device as disclosed herein configured to determine respiratory information of the subject from the thermal images; and an output interface configured to output the respiratory information of the subject.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device, in particular as defined in the dependent claims and as disclosed herein.

The present invention provides for an unobtrusive determination of respiratory information of an animal or human subject. As respiratory information, generally any information related to a respiratory (or breathing) characteristic may be determined, such as respiratory flow information, breathing effort information, obstructive apneas, central apneas, and mixed apneas. For instance, a signal indicative respiratory flow, in particular of the presence of respiratory flow, may be determined.

A thermal sensor unit, e.g. a 2D thermal sensor array such as a thermal camera (also called thermographic camera, infrared camera, thermal imaging camera or thermal imager) is used for this purpose. The invention is based on the idea that it is possible to discriminate between motion-induced thermal variations and breathing-flow induced thermal variations, as the motion-induced thermal variations (detected as respiratory motion pixels and/or pixel groups (a pixel group comprising a plurality of neighboring pixels)) occur on thermal gradients, and the breathing-flow induced thermal variations (detected as respiratory flow pixel or pixel groups) occur also in plain areas of the thermal image. For this discrimination of RR-frequent variations spatial filters can efficiently be used.

Although the motion-induced thermal variations (i.e., the time-varying values, or time-signal, of the respiratory motion pixels and/or pixel groups) can be helpful to establish the respiration rate, substantially eliminating the respiratory motion pixels and/or pixel groups exhibiting the motion-induced variations allows the determination of other respiratory information, such as a respiratory flow signal. This enables unobtrusive monitoring of a subject's respiration and respiratory effort, but also the detection of the presence and type of apnea, breathing cessation due to apnea, etc.

It shall be noted that the expression "pixels and/or pixel groups" shall be understood in the context of the present invention as (only) single pixels, or (only) pixel groups, or a mixture of pixels and pixel groups. A pixel group shall be understood a plurality of pixels, in particular a plurality of neighboring pixels. Generally, a pixel group may even contain a complete image, i.e., all pixels of an image. Thus, for instance, the feature that one or more spatial filters are applied to the respiratory pixels and/or pixel groups shall be understood such that it includes the option that one or more spatial filters are applied to single pixels, or to pixel groups, or to a mixture of pixel and pixel groups, or to a complete image (i.e. all pixels of an image).

In other words, a respiratory pixel group shall generally be understood as a group of pixels that exhibit respiratory information, i.e., their value varies over time in a pseudo-periodic way in a specific frequency range. Spatial filtering implies that pixels are combined with their spatially neighboring pixels, which need not (all) carry respiratory information. Moreover, sometimes it is easier to just spatially filter the entire image, and then evaluate the effect on the respiratory signal (time-variation of pixels).

According to a preferred embodiment the processing unit is configured to apply to the respiratory pixels and/or pixel groups at least two spatial filters, in particular at least two Gabor filters, having at least two different spatial filtering directions and/or one or more spatial frequencies. Depending on the situation two different spatial filters may be applied having two different spatial filtering directions and a common spatial frequency. In other embodiments two or more spatial filter with two or more different spatial frequencies may be applied.

Direction (or orientation) and spatial frequency are typical settings for spatial filters such as Gabor filters. By varying the direction/orientation it is possible to analyze variations in a thermal image from different orientations. Assuming that respiratory motion pixels are arranged in lines, applying a set of spatial filters that analyzes variations in the thermal image from different orientations, it can be expected that high responses are obtained in the filtering done in the orthogonal direction to the line, whereas the response to the filters in the other directions will be lower or even zero. The fact that respiratory flow pixels are arranged not in lines but in regions that seem more circular allows the assumption that the response to the spatial filters for respiratory flow can be considered independent of the direction of the filter. Therefore, a set of spatial filters is preferably applied, and then the responses may be multiplied together to automatically identify respiratory flow.

In another embodiment the processing unit is configured to identify, among the respiratory pixels and/or pixel groups, the respiratory motion pixels and/or pixel groups by use of the one or more spatial filters and to assume that the remaining pixels and/or pixel groups of the respiratory pixels and/or pixel groups are the respiratory flow pixels and/or pixel groups. This provides for a fast and efficient identification of the respiratory motion pixels and/or pixel groups. Generally, it may be possible to just use a single spatial filter, such as a 2D low-pass filter, and to compare the result with no filtering, so that effects may be seen in a respiratory motion signal, but not significantly in a respiratory flow signal.

In another embodiment the processing unit is configured to determine a respiration signal from the respiratory pixels and/or pixel groups and to eliminate or reduce contributions of the respiratory motion pixels and/or pixel groups to the respiration signal to obtain a respiratory flow signal as information on respiratory flow. As explained above, the use of one or more spatial filters allows to discriminate between respiratory motion and respiratory flow in the thermal images so that information on the respiratory flow (i.e. a signal that represents the breathing flow of the subject) can be determined by use of the present invention.

The processing unit may further be configured to determine the respiration signal by combining, in particular averaging, pixels and/or pixel groups that individually exhibit a temporal period or pseudo-periodic variation of pixel value in a respiration range or by selecting a pixel and/or pixel group that individually exhibits a temporal period or pseudo-periodic variation of pixel value in a respiration range. A single pixel having the best SNR may e.g. be selected for this purpose.

There are multiple options available for the processing unit about how to determine respiratory motion pixels and/or pixel groups and respiratory flow pixels and/or pixel groups. In an embodiment respiratory motion pixels and/or pixel groups are determined by detecting, from among the respiratory pixels and/or pixel groups, pixels and/or pixel groups that represent edges or temperature gradients in the obtained thermal images. In another embodiment respiratory flow pixels and/or pixel groups are determined by detecting, from among the respiratory pixels and/or pixel groups, pixels and/or pixel groups that do not represent edges or temperature gradients in the obtained thermal images. In still another embodiment respiratory motion pixels and/or pixel groups are determined as those respiratory pixels and/or pixel groups for which the spatial filtering of the thermal significantly changes the strength of a respiration signal and respiratory flow pixels and/or pixel groups are determined as those respiratory pixels and/or pixel groups for which the spatial filtering leaves the respiration signal substantially the same.

Edges of the thermal images identify regions and pixels which are close to substantial temperature changes. Respiratory motion in thermal videos is visible if there is contrast, which is present only if there is a difference in the detected temperature. Edges identify the pixels that are at the edge of a temperature difference. For instance, the face is at around 37° C. while the blanket is at around 30° C. so that the pixels at an edge between the face and the blanket will be identified as edges and can contain respiratory motion. The edges can be identified by using conventional edge detectors (detecting e.g. gradient as a feature). From a potential choice of pixels, all the pixels that are on the edges can then be removed to eliminate the contribution of the pixels that contain motion-induced breathing.

Although it is possible to completely eliminate the edge pixels to discard the motion-induced respiration, it is generally not necessary to eliminate non-moving edge pixels. If the strength of the temporal variations does not depend on the direction of the spatial filters, they are not motion-induced and they can be counted by the flow-induced respiratory pixels or pixel groups.

In another embodiment the processing unit is configured to determine respiratory flow pixel or pixel groups by determining one or more features of a set of features of the obtained thermal images, the set of features comprising:
   pseudo-periodicity indicating the height of a spectrum peak of a respiration pixel's signal,
   respiration rate cluster indicating cluster of pixels having similar frequencies,
   gradient indicating edges in thermal images,
   correlation indicating if the time domain signal of a pixel is correlated with the time domain signal of a respiratory pixel, and
   covariance indicating the covariance between the time domain signal of a pixel and the time domain signal of a respiratory flow pixel.

The processing unit may further be configured to determine a flow map by combining two or more of the features of the set of features and to apply one or more spatial filters to the flow map to determine the respiratory flow pixels and/or pixel groups. This provides for an efficient determination of respiratory flow pixels and/or pixel groups.

As mentioned already, various pieces of information related to respiration of the subject may be determined by use of the present invention. The processing unit may thus be configured to determine one or more of respiratory flow information, breathing effort information, obstructive apneas, central apneas, and mixed apneas, in particular to determine respiratory flow information representing respiratory flow of the subject by averaging the time domain signals of the respiratory flow pixels and/or pixel groups. It is generally possible to even determine other respiratory information, such a respiration rate.

In an embodiment the processing unit is particularly configured to detect respiratory motion pixels and/or pixel groups and to detect apnea of the subject based on the respiratory motion pixels and/or pixel groups and the respiratory flow pixels and/or pixel groups.

Another sensor unit, such as an RGB or NIR camera, may optionally be used in addition to sense second images for additional use in the determination of respiratory information. Accordingly, in an embodiment the image input is further configured to obtain second images of the subject obtained from emissions in the lower wavelength range than the emissions from which the thermal images are obtained, in particular in a wavelength range between 400 and 2000 nm such as visible or near-infrared light, the second images substantially showing at least part of the same region as the thermal images. The processing unit may then be configured to identify in the obtained second images respiratory motion pixels and/or pixel groups and to use the respiratory motion pixels and/or pixel groups identified in the obtained second images and the respiratory pixels and/or pixel groups identified in the obtained thermal images to determine the respiratory information.

Hereby, in a preferred embodiment, the processing unit may further configured to detect which of the respiratory pixels and/or pixel groups determined in the thermal images are absent in the second images and to determine, from among the respiratory pixels and/or pixel groups that are present in the thermal images but absent in the second images, the respiratory flow pixels and/or pixel groups.

The thermal sensor unit is preferably configured to sense emissions in a wavelength range of 2000 to 20000 nm, in particular in a wavelength range of 5000 to 20000 nm. A thermal camera or thermal sensor array may be used for this purpose.

An optional second sensor unit may be provided in an embodiment that is configured to sense emissions in a shorter wavelength range than the emissions from which the thermal images are obtained. Sensing emissions in a wavelength range between 400 and 2000 nm such as visible or near-infrared light is preferred to obtain second images of the subject from those emissions.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF THE INVENTION

Figure 1:
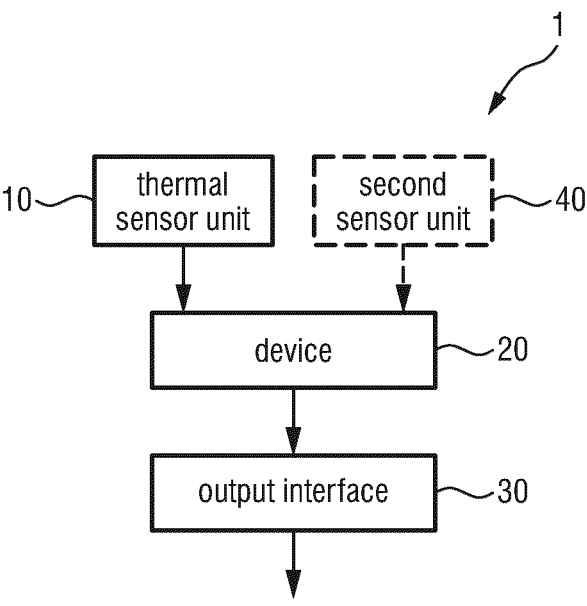
FIG. 1 shows a schematic diagram of an embodiment of a system according to the present invention.

FIG. 1 shows a schematic diagram of an embodiment of a system 1 for determining respiratory information of a subject according to the present invention. The subject may generally be any person, such as a patient, newborn, elderly person, in particular a person requiring close monitoring of respiration, such as a neonate, premature infant or patient with respiratory illness or insufficiency.

The respiratory information may generally be any information related to the subject's respiration. Of particular interest are one or more of respiratory flow information, breathing effort information, obstructive apneas, central apneas, mixed apneas and respiration rate. The determination of respiratory flow information representing respiratory flow of the subject and its discrimination from respiratory motion information representing respiratory motion of the subject is useful to determine the type of apnea, which may be important to decide if immediate action is required or not.

The system 1 is mainly used in a hospital environment, in an environment providing patient monitoring, or in another environment where the required equipment can be used or is already available. It may even be used at home where it may be useful to give the apparatus to a patient appearing at the family doctor with suspicions of sleep apnea. Trying the device for a few nights at home could help diagnosis.

The system 1 comprises a thermal sensor unit 10 configured to acquire thermal images of the subject, the thermal images showing at least part of the subject's facial area and/or its surrounding. For instance, the area of, or close to, the nose (in particular the nostrils) and/or mouth and neighboring area(s) (such a parts of a pillow, blanket, clothes next to nostrils and/or mouth) are of particular interest and shall be depicted in the thermal images. The thermal sensor unit 10 may generally be any means or unit that is able to acquire thermal images, such as a thermal camera or thermal sensor array, by sense emissions in a corresponding wavelength range, in particular in a wavelength range of 2000 to 20000 nm, preferably of 5000 to 20000 nm.

The system 1 further comprises a device 20 disclosed herein and described in the following for determining respiratory information of the subject from the thermal images. Details of the device 20 will be explained below.

The system 1 further comprises an output interface 30 configured to output the respiratory information of the subject. The output interface 30 may generally be any means or user interface that outputs information in visual or audible form, e.g. in text form, as image or diagram, as sound or spoken words, etc. For instance, the output interface 30 may be a display, a loudspeaker, a touchscreen, a computer monitor, the screen of a smartphone or tablet, etc.

The system 1 may further optionally comprise a second sensor unit 40 configured to sense emissions in a shorter wavelength range than the emissions from which the thermal images are obtained, in particular in a wavelength range between 400 and 2000 nm, such as visible or near-infrared light. From the emissions sensed by the second sensor unit 40 second images of the subject are generated, e.g. RGB or NIR images that may additionally be used in particular embodiments for the determination of the respiratory information. The second sensor unit 40 may thus e.g. be an RGB or NIR camera.

Figure 2:
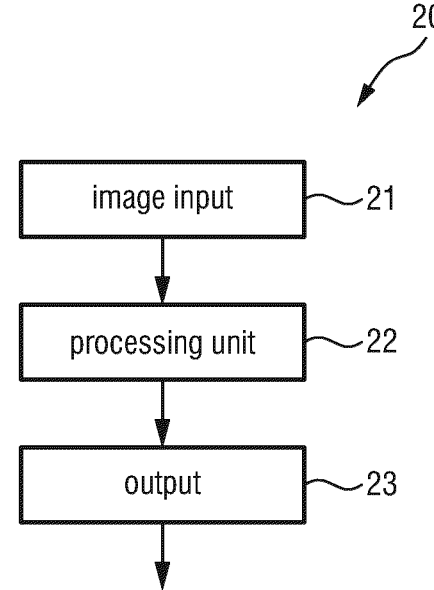
FIG. 2 shows a schematic diagram of an embodiment of a device according to the present invention.

FIG. 2 shows a schematic diagram of an embodiment of a device 20 according to the present invention.

The device 20 comprises an image input 21 configured to obtain thermal images of the subject, the thermal images showing at least part of the subject's facial area and/or its surrounding. The image input 21 may be directly coupled or connected to thermal sensor unit 10 (and, if available, the second sensor unit 40) or may obtain (i.e. retrieve or receive) the respective images from a storage, buffer, network, or bus, etc. The image input 21 may thus e.g. be a (wired or wireless) communication interface or data interface, such as a Bluetooth interface, WiFi interface, LAN interface, HDMI interface, direct cable connect, or any other suitable interface allowing signal transfer to the device 20.

The device 20 further comprises a processing unit 22 configured to determine respiratory information of the subject from the thermal images. The processing unit 22 may be any kind of means configured to process the images and determine respiratory information. It may be implemented in software and/or hardware, e.g. as a programmed processor or computer or app on a user device such as a smartphone, smartwatch, tablet, laptop, PC, workstation, etc.

The device 20 further comprises an output 23 configured to output the determined respiratory information of the subject. The output 24 may generally be any interface that provides the determined information, e.g. transmits it to another device or provides it for retrieval by another device (e.g. a smartphone, computer, tablet, etc.). It may thus generally be any (wired or wireless) communication or data interface.

Figure 3:
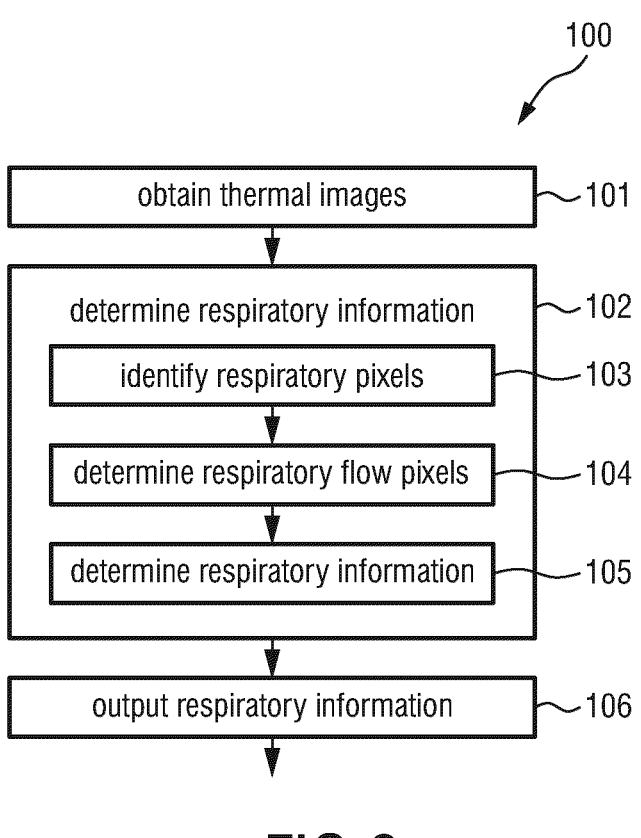
FIG. 3 shows a flowchart of an embodiment of a method according to the present invention.

FIG. 3 shows a flowchart of an embodiment of a method 100 according to the present invention. The steps of the method 100 may be carried out by the device 20, wherein the main steps of the method are carried out by the processing unit 22. The method may e.g. be implemented as computer program running on a computer or processor.

In a first step 101 thermal images of the subject are obtained. Optionally, in some embodiments second images (such as RGB or NIR images) are obtained in addition.

In a second step 102 respiratory information of the subject is determined from the thermal images. This includes several steps.

In step 103 respiratory pixels and/or pixel groups that show temperature variations related to respiration are identified in the obtained thermal images. In step 104, from among the respiratory pixels and/or pixel groups, respiratory flow pixels and/or pixel groups that show respiratory flow are determined. For this purpose one or more spatial filters, such as Gabor filters, are applied to the respiratory pixels and/or pixel groups to discriminate the respiratory flow pixels and/or pixel groups from respiratory motion pixels and/or pixel groups that show respiratory motion. In step 105 the desired respiratory information of the subject is determined from the respiratory flow pixels and/or pixel groups and/or the respiratory motion pixels and/or pixel groups.

In a final step 106 the determined respiratory information of the subject is output.

Figure 4:
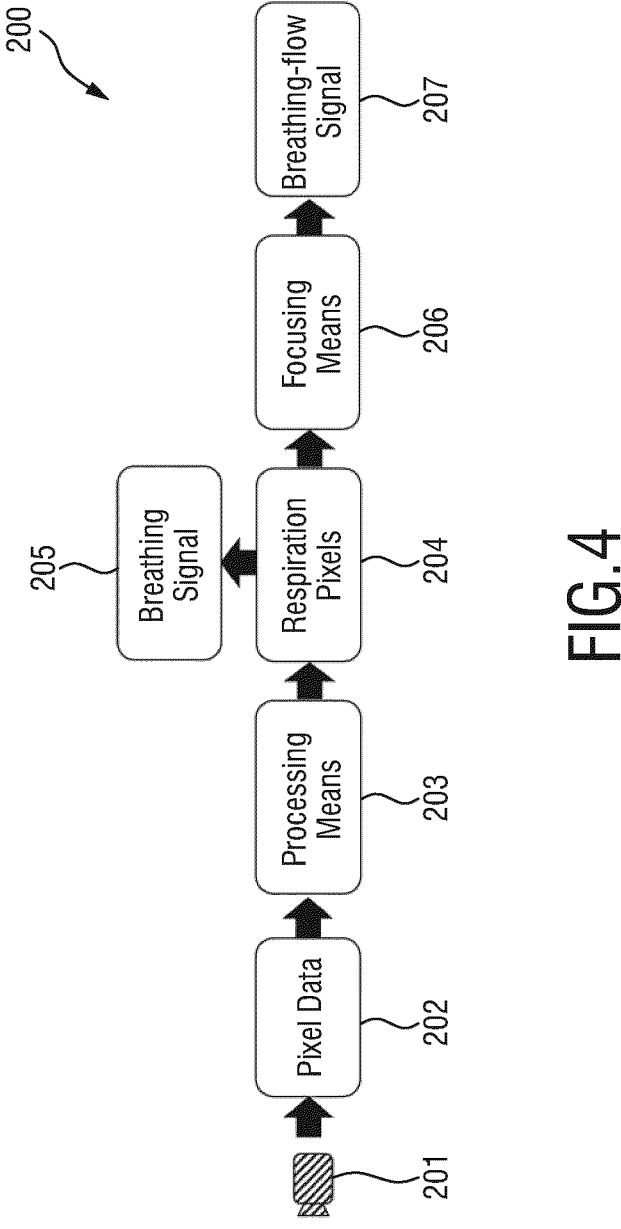
FIG. 4 shows a schematic diagram of another embodiment of a system according to the present invention.

FIG. 4 shows a schematic diagram of another embodiment of a system 200 according to the present invention. It comprises sensor means 201 (representing the thermal sensor unit 10 in the system 1) to unobtrusively capture emissions of at least part of a subject using e.g. a 2D array of thermal sensors and output pixel data 202. Processing means

203 and focusing means 206 are provided that implement the device 20 in the system 1, in particular its processing unit 22. The processing means 203 computes a breathing signal (respiration signal) 205 of the subject from the pixel data 203 of the sensor means 201, in particular from respiration pixels 204. The focusing means 206 reduces, or substantially eliminates, the contribution of pixels that contain motion-induced breathing from the breathing signal 205 and output the remaining breathing-flow signal (respiratory flow signal) 207.

In an embodiment an algorithm may be used to automatically identify the pixels containing respiration. The pixels containing the respiration signal can be located independent of their origin (respiratory motion or respiratory flow). An exemplary implementation of the algorithm uses one of more features, e.g. combines three features, to locate a core pixel, i.e., the pixel representing the subject's respiration (which may be motion-induced or flow-induced) with the highest quality according to a criterion. Example criteria can be amplitude, signal-to-noise ratio, spectral purity, skewness of the spectrum, etc. or a combination of several criteria. Then, based e.g. on a correlation of pixels with the core pixel, the respiratory pixels (or pixel groups) may be determined. The features are based on characteristics of the respiration signal and the respiratory pixels, respectively.

A first feature may be pseudo-periodicity. It generates a map in which each pixel value corresponds to the height of the normalized spectrum's peak. This map should identify the position of the pixels that contain a respiration signal based on the fact that respiration is periodic.

A second feature may be respiration rate clusters. It is based on the observation that respiration pixels are not isolated but arranged in clusters. A map is built in which each pixel value corresponds to the frequency of the spectrum's peak (e.g. pixel 1 value 50 breaths per minute). On this map a 2D non-linear filter is applied which gives higher weights if nearby pixels have similar frequencies.

A third feature may be gradient. This feature uses an edge detector to locate the edge of the thermal image since respiratory motion pixels are located only on edges. A standard edge detector can be used for this feature. In the case of the respiratory flow pixels the inverse of the gradient is used based on the knowledge that respiratory motion pixels are located on edges but respiratory flow pixels are mostly not located on the edges.

An optional fourth feature is correlation map. It is a map containing the pixels whose time domain signals have absolute correlation higher than 0.6 (or another set value) with the signal selected to be a respiration signal (extracted from what is called a core pixel). The core pixel is found as the pixel corresponding to the maximum value when multiplying pseudo-periodicity, respiration rate clusters, and gradient together. Therefore, correlation map is a binary map (0 and 1) where the 1 indicate the possible position of a respiration pixel. It is not known, however, if the pixel is a respiratory motion pixel or a respiratory flow pixel.

An optional fifth feature is covariance map. It is built when a flow-core pixel (i.e., a pixel which is most likely a respiratory flow pixel) is known. Once the covariance map is known, there will be pixels in anti-phase with the respiratory flow signal extracted from the flow-core pixel. These pixels are respiratory motion pixels (respiratory motion is present in two variants in thermal images: one is largely in phase with the flow signal and one is largely in anti-phase depending on the position on the pixels) which are eliminated from the possible selectable pixels. The respiratory flow pixels may exhibit an additional (smaller) phase shift caused by, and depending on, the heat capacity of the tissue or bedding which changes its temperature due to the respiratory flow.

By multiplying the features (in an example the first three features) together and selecting the pixels corresponding to the maximum value after the multiplication, the core pixel is found. This core pixel is then used to find all the other respiratory pixels based on correlation. The absolute value of the correlation coefficients obtained between the signal of the core pixel and all the other pixels' signals may be arranged into a 2D map called Correlation Map. The pixels that have an absolute correlation coefficient higher than a predetermined value, e.g. 0.7 or 0.8, are then used to generate a respiration signal by averaging them together.

Generally, a smaller (or larger) set of features can be used to build an input map for the spatial filters. However, due to the presence of noise and the difficulty in generalizing the solution for very different recordings a higher number of features ensures better results. One or more feature are used that find all the pixels containing respiration, which can be for example pseudo-periodicity or respiration rate clusters. From this set of pixels containing respiration the ones shall be found that contain respiratory flow. Once these pixels containing respiration are available, the spatial filter(s) or the inverse of the gradient can be applied to directly eliminate the respiratory motion. Therefore, at least two features are preferably used: one feature to find all the respiratory pixels, and one strategy or feature to find in these the respiratory flow pixels (e.g. using spatial filters or eliminating edges).

Figure 5:
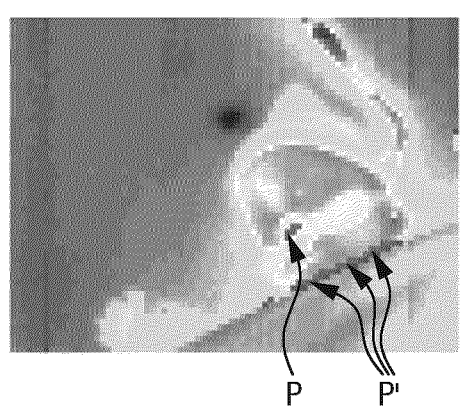
FIG. 5 shows an example image obtained from a real thermal video in which the pixels are automatically selected and a corresponding breathing signal.
Figure 5:
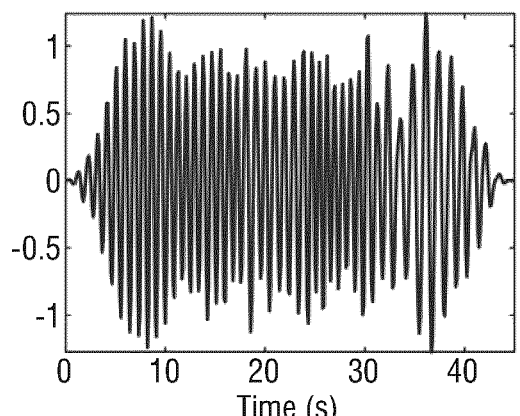
Figure 6:
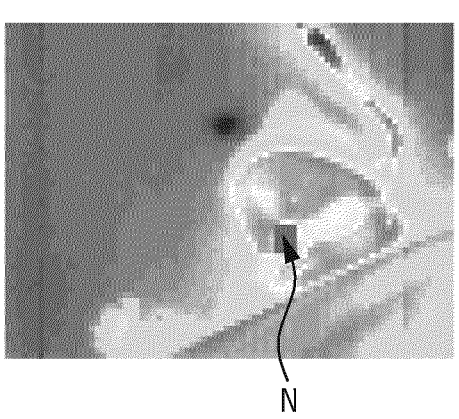
FIG. 6 shows the example image in which the region of the nostrils is manually selected and a corresponding breathing signal.
Figure 6:
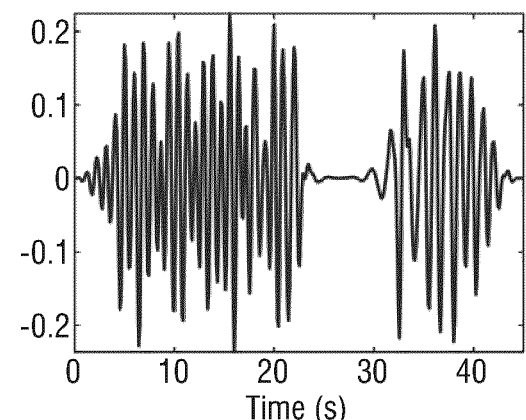
Figure 7:
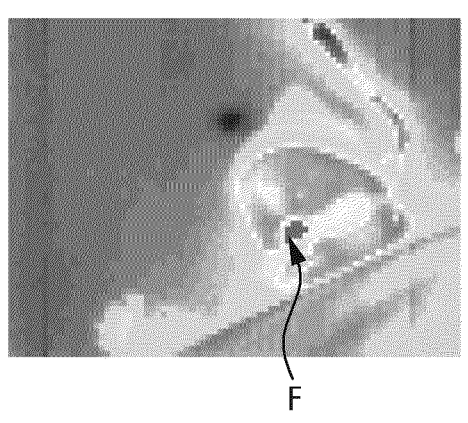
FIG. 7 shows a result obtained when applying features to a thermal video.
Figure 7:
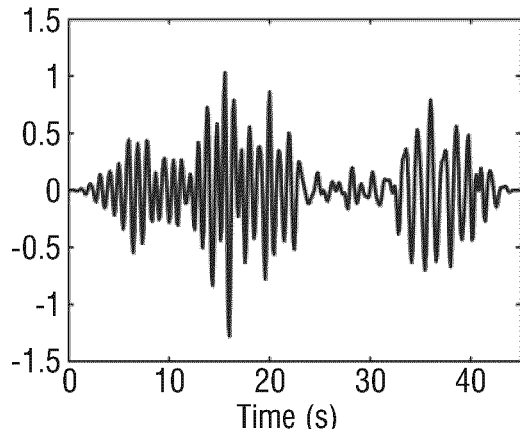

FIGS. 5 to 7 illustrates the idea of the invention by using a simulated obstructive apnea (flow absence and breathing effort still present) added to a real thermal video acquired on an infant.

FIG. 5 shows an example image obtained from a real thermal video in which the pixels are automatically selected (pixels at the nostrils are indicated by P; motion pixels at the edge between blanket and face are indicated by P'). Further, the breathing signal obtained from this image is shown. The manually added obstructive apnea is not detectable because respiratory motion pixels are also selected.

FIG. 6 shows the example image in which the region of the nostrils is manually selected (indicated by N). Further, the breathing signal obtained from this image is shown, which proves that the obstructive apnea is present and is generally detectable.

Combining information related to the respiratory motion pixels and respiratory flow pixels, features that focus on the detection of solely flow pixels can be built. FIG. 7 shows the result obtained when applying these features to a thermal video. The pixels automatically selected (indicated by F) concern only the flow area, in contrast with the pixels P automatically selected in FIG. 5. In this case the simulated obstructive apnea is visible and can be detected using the present invention.

More specifically, this exemplary result was obtained by applying a bank of Gabor filters to the correlation map obtained before. Through the multiplication of all the responses to the Gabor filters together, parts of the correlation map are amplified which are independent of the orientations of the filters. The respiratory flow pixels can therefore automatically identified.

Other embodiments may identify the pixels containing flow using optics to focus only on the nostrils area or by positioning the camera close to the nostrils. This may be quite complex as it may require detecting the nostrils area in the first place or the closeness with the camera may be uncomfortable for the subject. Moreover, a much stronger flow-signal may be present in thermal images at other places, e.g. on the pillow close to the nose of the subject. These stronger signals cannot be profited from when using a nostril detector, while they can be used according to the present invention to get a much stronger SNR or to allow flow detection while the nostrils are invisible.

In another exemplary implementation of the present invention the identification of the respiratory flow pixels (also called RF pixels in the following) is based on five features, partially already described above, combined with a new use of a bank of Gabor filters. These filters allow exploiting the characteristic of RF pixels, i.e., that they typically occur in 2D-smooth areas. Using the chosen pixels, an RF signal and the flow-based respiration rate (RR) can be obtained.

Moreover, obstructive apneas were simulated in a plurality of video segments and a known method for the detection of cessations of breathing (COBs) was used (as described in Lorato, I.; Stuijk, S.; Meftah, M.; Verkruijsse, W.; de Haan, G. Camera-Based On-Line Short Cessation of Breathing Detection. 2019 IEEE/CVF International Conference on Computer Vision Workshop (ICCVW). IEEE, 2019, pp. 1656-1663). This allows comparing the detectability of the obstructive apneas in the different respiration signals obtained from the thermal videos (i.e. mixed respiration signal (MR signal, i.e. a respiratory signal coming from both RF and respiratory motion (RM)) and RF signal).

Figure 8:
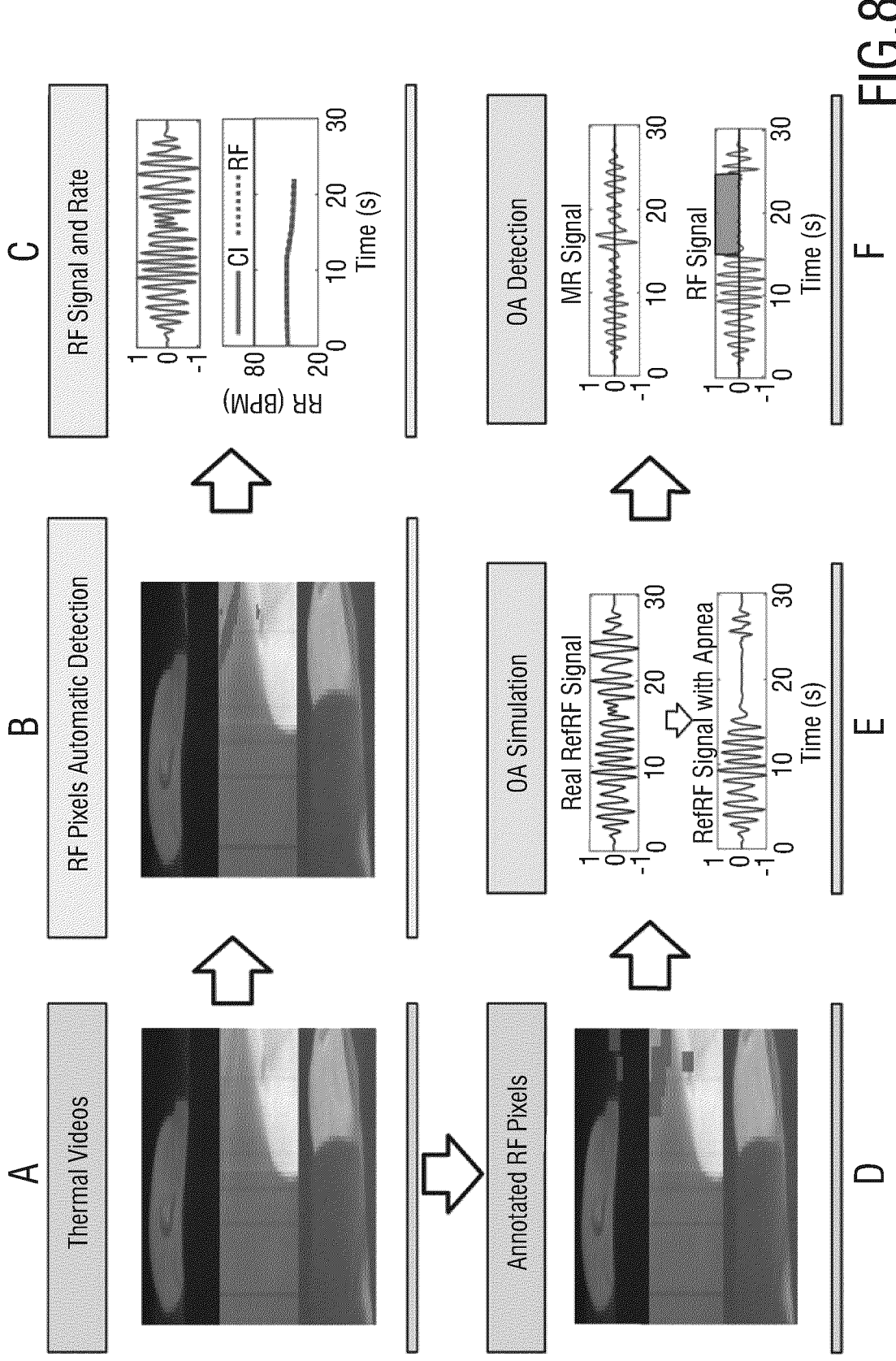
FIG. 8 shows a schematic diagram of the concept of an embodiment of the present invention.

These steps are summarized in FIG. 8 showing a schematic diagram of the concept of an embodiment of the present invention. RF pixels are automatically detected (FIG. 8B) in the thermal videos (FIG. 8A) and used to calculate the RF signal and the flow-based RR (FIG. 8C). Moreover, the RF pixels' location is manually annotated (FIG. 8D). The annotated RF pixels are substituted with noise to simulate the occurrence of an OA (FIG. 8E). A COB-detector is used to compare the performance in OA detectability between the RF signal and the MR signal (FIG. 8F). An exemplary implementation will be explained in the following.

Initially, preprocessing is performed. The thermal images coming from one or more camera views, e.g. three camera views, are merged on the same image plane and as visible in FIG. 8A, obtaining a single video with resolution 180×80, i.e. M×L. Each pixel time domain signal was interpolated with a 1D linear interpolation to compensate for the uneven sampling rate. The resulting frame rate is 9 Hz, close to the average frame rate of an infrared camera.

In the next step respiratory flow detection is performed. For the automatic detection of RF pixels an embodiment explained above may be used. In an embodiment, a set of e.g. five features (three of which have been explained above already; more or fewer features may be used in other embodiments) may be combined to identify the RF pixels. A flow-core pixel, i.e., a pixel that is most likely to belong to the RF pixels (a pixel representing the subject's respiratory flow with the highest quality according to a criterion; it may be that there exists a pixels that represents motion-induced respiration with an even higher score on that criterion), is selected as it will be used as a basis for the calculation of one of the features. Spatial filters (e.g. Gabor filters) are used for the accurate selection of the flow-core pixel. The time domain signals of each pixel in each window are referred to as $x_{m,l}(nT_s)$, where (m, l) indicates the pixel position, and $n=0+(j-1)/T_s$, $1+(j-1)/T_s$, . . . , $N+(j-1)/T_s$. In an exemplary implementation each window is identified by the integer j, and consists of N=72 consecutive samples in an 8 s fragment, sliding in steps of 1 s. The sampling period $T_s$ equals $T_s=0.111$ s.

Gabor filters are well-known bandpass filters used in image processing for texture and edge detection. The kernel is formed by a sinusoidal carrier and a 2D Gaussian envelope. Several Gabor filters can be generated by varying the spatial frequency of the sine wave and the orientation of the filter. By applying a set of filters to an image, edges and textures can be emphasized. Considering the properties of the distribution of RF pixels and RM pixels, a bank of Gabor filters may be applied by varying the orientation and/or the spatial frequency aiming at locating flow pixels, which should have a similar response for all orientations. For RM pixels, on the other hand, a higher response is expected in specific directions, being mostly along, possibly curved, lines. A set of parameters may be empirically selected for the orientation and for the spatial frequency of the filters, $\lambda=3$, $4$, . . . , $8$ pixels/cycle and $\theta=10°$, $20°$, $30°$, . . . , $170°$. Multiple spatial frequencies may be chosen to allow the method to work with both flow visible at nostrils/mouth and/or flow visible on textiles, as these usually produce regions affected by flow with different sizes.

The bank of Gabor filters is applied to an input map called Flow Map, which will be defined below, by convolving the input map with each Gabor filter. In particular:

$$\Psi(\lambda, \theta) = |\vec{FM} \otimes \Gamma(\lambda, \theta)|, \tag{1}$$

where $\Gamma(\lambda, \theta)$ represent a Gabor filter, and FM is the input map. The $\Psi(\lambda, \theta)$ are the magnitudes of the Gabor responses for each spatial frequency and orientation $\theta$. The flow-core pixel may be selected by multiplying all the Gabor responses $\Psi(\lambda, \theta)$. The flow-core pixel is the pixel corresponding to the highest value in the image resulting from the multiplication:

$$\left(m_{p_f}, l_{p_f}\right) = \underset{(m,l)}{\operatorname{argmax}}\left(\prod_{\lambda,\theta}\Psi(\lambda, \theta)\right). \tag{2}$$

Therefore, $(m_{pf}, l_{pf})$ indicates the position of the flow-core pixel in each window. The map given as input to the Gabor filters is called Flow Map and is a combination of five features. In particular:

$$FM = \hat{C} \cdot \tilde{C}_{flow} \cdot \tilde{Q} \cdot \tilde{W} \cdot (J - G). \tag{3}$$

$\tilde{C}flow$ is a new feature introduced to locate RF pixels more accurately, which is called Covariance Map. Each element represents the covariance between the signal of the flow-core pixel found in the previous window and the signal of the other pixels in the video segment. $\tilde{C}flow$ is the normalized version of the Covariance Map:

$$c_{flow_{m,l}} = \begin{cases} 1 & \text{if } j = 1 \\ \frac{1}{N}\sum_{t=1}^{N} \hat{x}_{\left(m_{p_f}, l_{p_f}\right)_{j-1}}(t) \cdot \hat{x}_{m,l}(t) & \text{otherwise} \end{cases}. \tag{4}$$

$C_{flow_{m,l}}$ represents, therefore, the covariance between the signal of the chosen flow-core pixel in the previous window $(m_{pf}, l_{pf})_{j-1}$ and the signal of a pixel in position (m, l).

$\hat{x}(mp_f,lp_f)_{j-1}$ (t) and $\hat{x}_{m,l}(t)$ are the filtered time domain signals, while t is an index that sweeps through the samples in the jth window. The time domain signals are filtered with a pass-band between 30 and 110 breaths per minute (BPM), i.e., the expected breathing frequency range of an infant. The $C_{flow_{m,l}}$ are then normalized resulting in a matrix between −1 and 1, i.e. $\tilde{C}_{Flow}$. The covariance is preferred to the correlation coefficient because it allows taking into consideration also the standard deviation of the time signals, which is advantageous assuming the biggest thermal variations are associated with respiration. Moreover, the sign of the covariance is kept which allows rejecting anti-phase signals, which can only originate from motion.

The other four features in equation (3) are developed to obtain a MR signal from thermal videos. All the features have been explained above as first to fifth features (pseudo-periodicity, respiration rate clusters, gradient, correlation map, covariance map).

These features are designed to locate MR pixels but can be adapted for the identification of the RF pixels. Q is called Pseudo-periodicity and is based on the estimation of the height of the normalized spectrum's peak. W is called RR Clusters and is based on the application of a 2D non-linear filter for the detection of pixels that have similar frequencies nearby. G is Gradient, which identifies the edges of the thermal images. These three features may be used to identify a core pixel, i.e. a pixel that best represents the MR signal. Once a core pixel is found a Pearson correlation coefficient may be used to locate all the other pixels containing respiration signals. The MR signal is obtained by averaging these pixels together. The Pearson correlation coefficients obtained between the core pixel and all the other pixels are arranged in the Correlation Map and indicated with C. The Correlation Map obtained from the core pixel can be used to locate the MR pixels. This map is binarized by applying an empirical threshold $\zeta_1$ on the absolute values equal to 0.6:

$$\hat{C} = |C| > \zeta_1. \tag{5}$$

The Flow Map can be obtained by combining this binarized Correlation Map with the Covariance Map and the other features as explained above in equation (3). $\tilde{Q}$, $\tilde{W}$, and G represent the Pseudo-periodicity, RR Clusters, and Gradient features respectively, the tilde is used to indicate that the features were normalized between 0 and 1, G is already binary. J is an M×L matrix containing all ones, and therefore the combination with the Gradient feature gives a weight equal to 1 to the non-edge regions. The Flow Map was then binarized by applying an empirical threshold, $\zeta_2$ equal to 0.2:

$$\widehat{FM} = FM > \zeta_2. \tag{6}$$

Even though the combination of these features allows removing most of the RM pixels from the selectable pixels, in the first window the Covariance Map is not computed and some of these pixels may still be present in the binarized Flow Map. Moreover, considering the flow-core pixel is used to estimate the Covariance Map in the following windows, the detection of the right pixel is particularly important. Additionally, the Flow Map may still contain some noise-pixels as well as the flow, ones. Therefore, to select the flow-core pixel accurately, the bank of Gabor filters is introduced, and the $\widehat{FM}$ is given as input to the bank, as done in Equation (1).

The RF pixels are therefore detected, in the first window of each video segment only the flow-core-pixel is used, afterwards, all non-zero pixels in $\widehat{FM}$ are considered RF pixels:

$$P_{flow} = \begin{cases} \left(m_{P_f}, l_{P_f}\right) & \text{if } j = 1 \\ (m, l): \widehat{FM}(m, l) = 1 & \text{otherwise} \end{cases} \tag{7}$$

Figure 9:
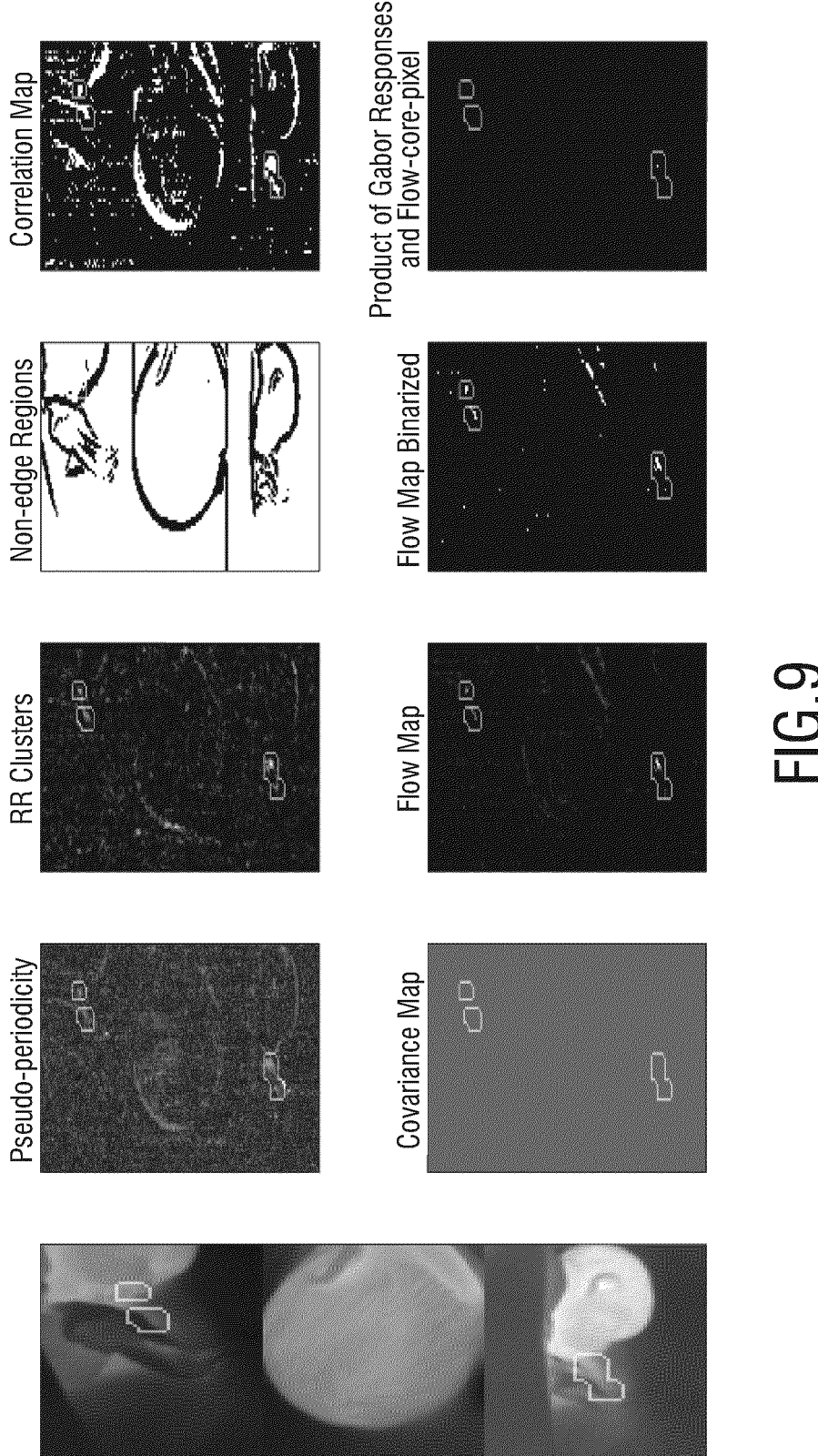
FIG. 9 shows three thermal images and an example of features in a first window.
Figure 10:
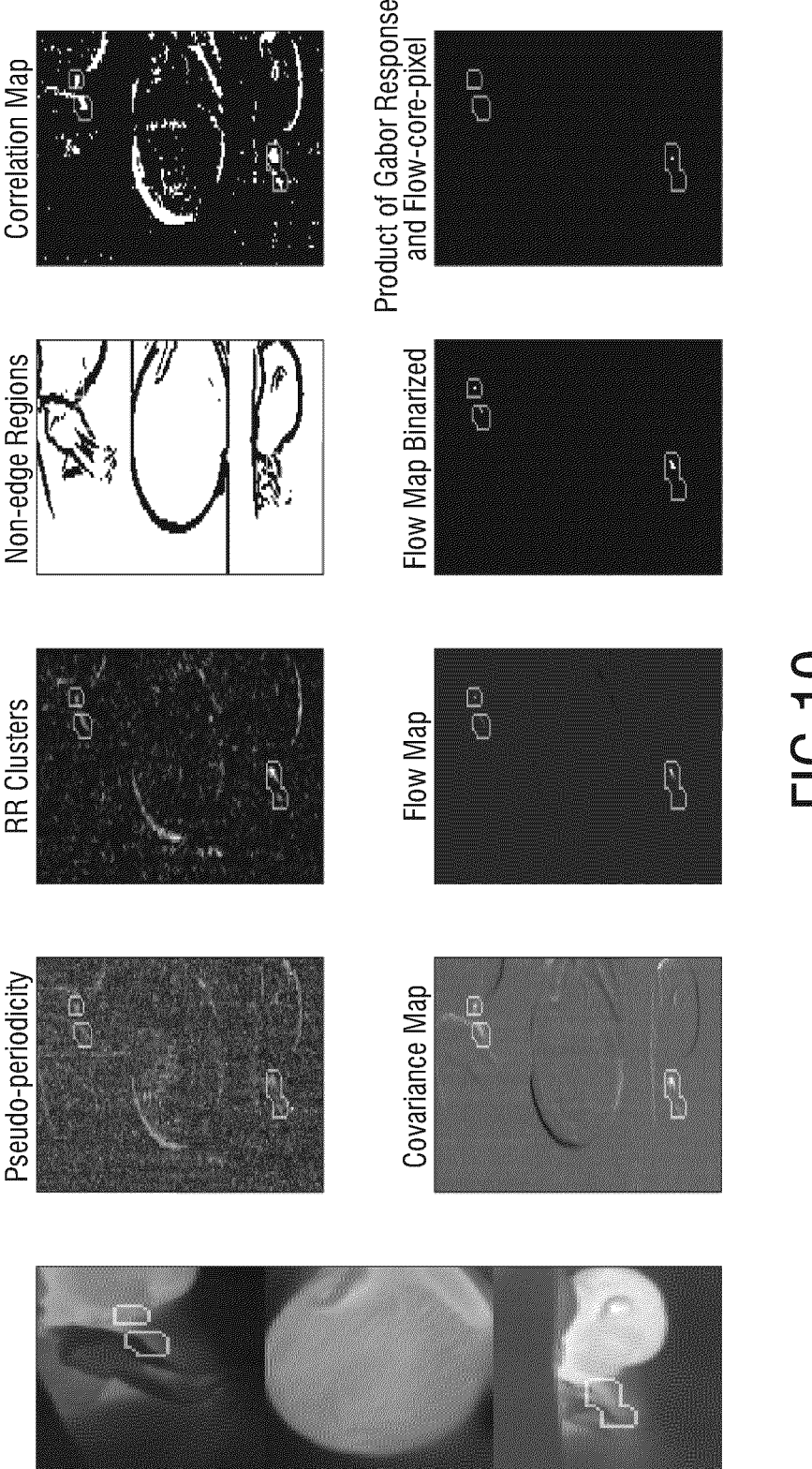
FIG. 10 shows the three thermal images and an example of features in a subsequent window.

$P_{flow}$ is, therefore, a set containing the positions of the detected RF pixels. The conditions for RF pixels detection are quite strict. It could happen that no pixel is found. In that case the previously chosen RF pixels are used in the current window as well. The RF signal is obtained by averaging together all RF pixels contained in $P_{flow}$. An example of the features in the first window is shown in FIG. 9. The features obtained in the following window are shown in FIG. 10. In these figures the location of the annotated RF pixels is indicated with a perimeter. FIGS. 9 and 10 show the advantage introduced by the use of the Covariance Map, rejecting anti-phase RM pixels. As a consequence the Flow Map shown in FIG. 10 does not contain RM pixels compared to the Flow Map shown in FIG. 9. The MR signal is also obtained from the videos and will be used for comparison purposes.

In a next step obstructive apnea detection may be performed. A COB detector (as e.g. disclosed in the document of Lorato, I.; Stuijk, et al. mentioned above) may be used to evaluate the detectability of obstructive apneas, which were simulated as indicated in above. The COB detector assumes that COBs can be detected by monitoring sudden amplitude changes and is based on the comparison of a short-term standard deviation and a long-term standard deviation. Adaptations may be made to the COB detector concerning the length of the windows for the calculation of the two standard deviations. The duration of these windows may generally be chosen based on the targeted COB. In particular, the window for the calculation of the short-term standard deviation may be close to the minimum COB duration, an apnea of 10 s, whereas the window for the long-term standard deviation, which is calculated as median of the short-term standard deviations, may be higher than the COB duration. Otherwise, the long-term standard deviation will dynamically adapt to the standard deviation during the apnea event (i.e. detecting the cessation of the event while the apnea is still ongoing). In another implementation, the short-term standard deviation is calculated using 8 s windows, which is the same sliding window approach used for the RR estimation. The long-term standard deviation is calculated in a window of 15 s (other periods may be applied as well). This window could be reduced to 11 s considering the fact that this is closer to the designed duration of the obstructive apnea, but it may be kept higher to easily adapt to non-simulated cases.

The RF signal and MR signal are obtained as described above using e.g. a dataset with simulated obstructive apneas. The COB detector is applied to a Reference RF (RefRF) signal (obtained by averaging together all the annotated RF pixels), as reference of the results achievable when monitoring RF, on the RF signal obtained from applying the proposed method, and also on the MR signal to highlight the limitations of monitoring this type of signal when aiming at apnea detection.

In another embodiment in addition to the thermal sensor unit (also called first sensor unit) a second sensor unit (40; see FIG. 1), such as an optical camera, registering substantially the same scene including the subject may be used. The idea is that a thermal camera registers both respiratory flow and respiratory motion, while an optical camera can only register respiratory motion. A combination allows for a separation of the two respiratory signals.

Although the motion-induced thermal variations can be helpful to establish the breathing rate from a thermal camera, substantially eliminating the pixels exhibiting the motion-induced variations using the data from the optical camera allows the measurement of the respiratory flow signal (provided it is present in the captured image, which may depend on the view of the cameras; multiple cameras viewing the subject from multiple angles may be used to ensure visibility of respiratory flow). In addition, irradiation means (e.g. dedicated illumination means or just ambient light) may be used to irradiate the subject with radiation in a wavelength range captured by the second sensor unit.

The processing unit (22 in FIG. 2) of the device may be configured in such an embodiment to determine corresponding pixel data between pixels from the first and second sensor units, and look for image regions in the thermal images that exhibit breathing information which are absent in the corresponding regions in the second images acquired by the second sensor unit. By computing a respiration signal based only on those pixels the respiratory flow may be computed.

The first and second sensor units may be oriented such that they capture the same part of the scene including the same part of the subject. In case there is a necessary parallax between their views, image registration techniques may be used to align the images to define corresponding pixels.

Although thermal and optical imagers both allow detection of respiratory motion, and both typically find this motion on edges in their respective image, it is to be taken into account that an optical camera usually finds many more image edges than a thermal camera does. A thermal image typically has little detail, and strong edges mainly occur at the boundary of the subject and his/her environment. An optical camera will typically also "see" these edges, but registers many more edges as the optical reflections provide an image that is much richer in detail.

Consequently, although respiratory flow may be available in relatively flat regions of the thermal image, significant detail may still exist in the optical image. When removing pixels from detailed regions, too many pixels may be removed from the thermal image from regions containing respiratory flow only. However, the pixels that remain are in a flat optical area, which should almost certainly be a flat thermal region. If respiratory flow occurs in such regions of the thermal image, then those pixels can be used to output the (initial) respiratory flow signal.

A further consequence is that since likely few pixels can be used from the thermal image, the threat exists that the resulting signal has a poor signal-to-noise-ratio (SNR). This can be prevented though by recognizing that flow and motion based thermal variations also differ in phase and shape of the signal. A core pixel, i.e. the pixel that exhibits the strongest pseudo-periodical signal to find pixels with a similar (phase and shape, using correlation), may be used, and the core pixel may be combined with similar pixels to obtain a robust (high SNR) respiration signal. The core pixel typically has respiratory motion as this is often stronger. The combined pixels of the "initial respiration signal" can be used as a new "core pixel" to find similar pixels to combine with for improved SNR of the respiratory flow output signal.

The proposed device, system and method obtained promising results in the automatic identification of respiratory flow pixels in thermal videos and in obtaining RF signals. Further, they enable determination of different types of respiratory information, in particular the detection of apneas and the type of apneas.

Practical implementations should aim at maximizing RF visibility in thermal videos. An array of cameras could be used to ensure the visibility of the mouth and/or nostrils area in the videos. Moreover, the subject should preferably be in supine position.

The present invention may be applied for patient monitoring, in particular in unobtrusive vital signs monitoring. It may be used in various scenarios and environments, such as (but not limited to) hospitals, specialized sleep centres and home (baby) care.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for determining respiratory information of a subject, the device comprising:
an image input that is configured to obtain thermal image data of the subject, the thermal image data including data associated with at least a portion of the subject's facial area and/or its surrounding;
a processor configured to determine the respiratory information of the subject from the thermal image data; and
an output that is configured to output the respiratory information of the subject,
wherein the processor is configured to determine the respiratory information of the subject by:
identifying, in the thermal image data, thermal image respiratory pixels and/or pixel groups indicative of a temperature variation related to respiration,
determining, from among the thermal image respiratory pixels and/or pixel groups, respiratory flow pixels and/or pixel groups indicative of a respiratory flow,
applying one or more spatial filters of the processor to the thermal image respiratory pixels and/or pixel groups to discriminate the respiratory flow pixels and/or pixel groups from respiratory motion pixels and/or pixel groups indicative of a respiratory motion, and

determining the respiratory information of the subject from the respiratory flow pixels and/or pixel groups and/or the respiratory motion pixels and/or pixel groups.

2. The device as claimed in claim 1,
wherein the processor is configured to apply at least two spatial filters of the one or more spatial filters to the thermal image respiratory pixels and/or pixel groups.

3. The device as claimed in claim 2, wherein the at least two spatial filters include at least two Gabor filters, having at least two different spatial filtering directions and/or one or more spatial frequencies.

4. The device as claimed in claim 1,
wherein applying the one or more spatial filters of the processor to the thermal image respiratory pixels and/or pixel groups identifies the respiratory motion pixels and/or pixel groups, while pixels and/or pixel groups of the thermal image respiratory pixels and/or pixel groups that remain upon filtering are the respiratory flow pixels and/or pixel groups.

5. The device as claimed in claim 1,
wherein the processor is configured to determine a respiration signal from the thermal image respiratory pixels and/or pixel groups and to eliminate or reduce contributions of the respiratory motion pixels and/or pixel groups to the respiration signal to obtain a respiratory flow signal as information on respiratory flow.

6. The device as claimed in claim 5,
wherein the processor is configured to determine the respiration signal by averaging the thermal image respiratory pixels and/or pixel groups that individually exhibit a temporal period or pseudo-periodic variation of pixel value in a respiration range or by selecting a pixel and/or pixel group from the thermal image respiratory pixel and/or pixel groups that exhibits a temporal period or pseudo-periodic variation of pixel value in a respiration range.

7. The device as claimed in claim 1,
wherein the processor is configured to:
determine respiratory motion pixels and/or pixel groups by detecting, from among the thermal image respiratory pixels and/or pixel groups, pixels and/or pixel groups that represent edges or temperature gradients in the obtained thermal image data, and/or
determine respiratory flow pixels and/or pixel groups by detecting, from among the thermal image respiratory pixels and/or pixel groups, pixels and/or pixel groups that do not represent edges or temperature gradients in the obtained thermal image data, and/or
determine respiratory motion pixels and/or pixel groups as those respiratory pixels and/or pixel groups, wherein the spatial filtering of the thermal image changes intensity of a respiration signal and to determine respiratory flow pixels and/or pixel groups as those respiratory pixels and/or pixel groups, wherein the spatial filtering leaves the respiration signal substantially the same.

8. The device as claimed in claim 1, wherein the processor is configured to
determine respiratory flow pixel or pixel groups by determining one or more features of a set of features of the obtained thermal image data, the set of features comprising:
a pseudo-periodicity indicating the height of a spectrum peak of a respiration pixel's signal,
a respiration rate cluster indicating cluster of pixels having similar frequencies,

a gradient indicating one or more edges in thermal image data,
a correlation indicating if a time domain signal of a pixel is correlated with a time domain signal of a respiratory pixel, and
a covariance indicating the covariance between the time domain signal of the pixel and the time domain signal of the respiratory flow pixel.

9. The device as claimed in claim 8,
wherein the processor is configured to determine a flow map by combining two or more of the features of the set of features and to apply the one or more spatial filters to the flow map to determine the respiratory flow pixels and/or pixel groups.

10. The device as claimed in claim 1,
wherein the processor is configured to determine one or more of respiratory flow information, breathing effort information, obstructive apneas, central apneas, and mixed apneas.

11. The device as claimed in claim 10, wherein the one or more of respiratory flow information is determined by averaging time domain signals of the respiratory flow pixels and/or pixel groups.

12. A device as claimed in claim 1,
wherein the processor is further configured to:
detect respiratory motion pixels and/or pixel groups; and
detect apnea of the subject based on the respiratory motion pixels and/or pixel groups and the respiratory flow pixels and/or pixel groups.

13. A device as claimed in claim 1,
wherein the image input is further configured to obtain second image data of a second image of the subject obtained from emissions in the shorter wavelength range than the emissions from which the thermal image data is obtained, in a wavelength range between 400 and 2000 nm such as visible or near-infrared light, the second image data including data associated with at least part of the same region of the subject as the thermal image data, and
wherein the processor is further configured to identify, in the second image, respiratory motion pixels and/or pixel groups and to use the respiratory motion pixels and/or pixel groups identified in the second image data and the thermal image respiratory pixels and/or pixel groups identified in the thermal image data to determine the respiratory information.

14. The device as claimed in claim 13,
wherein the processor is further configured to detect which of the thermal image respiratory pixels and/or pixel groups determined in the thermal image data are absent in the second image data and to determine, from among the thermal image respiratory pixels and/or pixel groups that are present in the thermal image data but absent in the second image data, the respiratory flow pixels and/or pixel groups.

15. A system for determining respiratory information of a subject, the system comprising:
a thermal sensor configured to acquire thermal image data associated with the subject, the thermal image data including data associated with at least a part of the subject's facial area and/or its surrounding;
a device comprising:
an image input that is configured to obtain thermal image data via the thermal sensor, the thermal image data including data associated with at least a portion of the subject's facial area and/or its surrounding;

a processor configured to determine the respiratory information of the subject from the thermal image data, wherein the processor is configured to determine the respiratory information of the subject by:

identifying, in the thermal image data, thermal image respiratory pixels and/or pixel groups indicative of a temperature variation related to respiration, determining, from among the thermal image respiratory pixels and/or pixel groups, respiratory flow pixels and/or pixel groups indicative of a respiratory flow, applying one or more spatial filters of the processor to the thermal image respiratory pixels and/or pixel groups to discriminate the respiratory flow pixels and/or pixel groups from respiratory motion pixels and/or pixel groups indicative of a respiratory motion, and determining the respiratory information of the subject from the respiratory flow pixels and/or pixel groups and/or the respiratory motion pixels and/or pixel groups; and an output interface that is configured to output the respiratory information of the subject.

16. The system as claimed in claim 15, wherein the one or more spatial filters comprise at least two spatial filters.

17. The system as claimed in claim 16, wherein the at least two spatial filters include at least two Gabor filters, having at least two different spatial filtering directions and/or one or more spatial frequencies.

18. The system as claimed in claim 15, wherein applying the one or more spatial filters of the processor to the thermal image data respiratory pixels and/or pixel groups identifies the respiratory motion pixels and/or pixel groups while pixels and/or pixel groups of the respiratory pixels and/or pixel groups that remain upon filtering are the respiratory flow pixels and/or pixel groups.

19. A method for determining respiratory information of a subject, the method comprising:

obtaining thermal image data of the subject, the thermal image data associated with at least part of the subject's facial area and/or its surrounding;

determining the respiratory information of the subject from the thermal image data; and outputting the respiratory information of the subject, wherein the respiratory information of the subject is determined by:

identifying in the thermal image data, respiratory pixels and/or pixel groups indicating temperature variations related to respiration, determining, from among the thermal image data respiratory pixels and/or pixel groups, respiratory flow pixels and/or pixel groups indicative of respiratory flow;

applying one or more spatial filters to the thermal image data respiratory pixels and/or pixel groups to discriminate the respiratory flow pixels and/or pixel groups from respiratory motion pixels and/or pixel groups that show respiratory motion, and determining the respiratory information of the subject from the respiratory flow pixels and/or pixel groups and/or the respiratory motion pixels and/or pixel groups.

20. A non-transitory computer readable medium comprising a computer code for causing a computer to carry out the steps of the method as claimed in claim 19.

* * * * *